(12) United States Patent
Hashman et al.

(10) Patent No.: US 9,447,376 B2
(45) Date of Patent: Sep. 20, 2016

(54) DRIED SPORE GERMINATIVE COMPOUND MIXTURES

(71) Applicant: Envera, LLC, West Chester, PA (US)

(72) Inventors: Tommie Eugene Hashman, West Chester, PA (US); Michael Matheny, Landenberg, PA (US)

(73) Assignee: Envera, LLC, West Chester, PA (US)

( * ) Notice: Subject to any disclaimer, the term of this patent is extended or adjusted under 35 U.S.C. 154(b) by 0 days.

(21) Appl. No.: 14/174,099

(22) Filed: Feb. 6, 2014

(65) Prior Publication Data

US 2014/0220662 A1     Aug. 7, 2014

Related U.S. Application Data

(60) Provisional application No. 61/849,973, filed on Feb. 6, 2013.

(51) Int. Cl.
*C12N 1/20* (2006.01)

(52) U.S. Cl.
CPC ........................ *C12N 1/20* (2013.01)

(58) Field of Classification Search
None
See application file for complete search history.

(56) References Cited

U.S. PATENT DOCUMENTS

| 2003/0124104 A1 | 7/2003 | Farmer |
| 2011/0033436 A1 | 2/2011 | Chen et al. |
| 2014/0295482 A1* | 10/2014 | Lyte ............................... 435/29 |

FOREIGN PATENT DOCUMENTS

| WO | WO-95/25163 A1 | 9/1995 |
| WO | WO-99/05310 A1 | 2/1999 |
| WO | WO-2010/070005 A1 | 6/2010 |
| WO | WO-2012/087980 A1 | 6/2012 |

OTHER PUBLICATIONS

Yi et al., "Studies of the Commitment Step in the Germination of Spores of *Bacillus* Species", Journal of Bacteriology 2010, vol. 192, pp. 3424-3433.*
Paredes-Sabja et al., "Germination of spores of *Bacillales* and *Clostridiales* species: mechanisms and proteins involved", Trends in Microbiology 2011, vol. 19, pp. 85-94.*
International Search Report for PCT/US2014/015076, mailed Apr. 28, 2014.
Russell, "Bacterial Spores and Chemical Sporicidal Agents", Clinical Microbiol. Rev., 1990, vol. 3, No. 2, pp. 99-119.
Atluri et al., "Cooperativity Between Different Nutrient Receptors in Germination of Spores of *Bacillus subtilis* and Reduction of This Cooperativity by Alterations in the GerB Receptor", Journal of Bacteriology, 2006, vol. 188, No. 1, pp. 28-36.
Blocher et al., "Inhibition of Germinant Binding by Bacterial Spores in Acidic Environments", Applied and Environmental Microbiology, 1985, vol. 50, No. 2, pp. 274-279.
Foerster et al., "Endotrophic Calcium, Strontium, and Barium Spores of *Bacillus megaerium* and *Bacillus cereus*", Journal of Bacteriology, 1966, vol. 91, No. 3, pp. 1333-1345.
Cartman et al., "*Bacillus subtilis* Spores Germinate in the Chicken Gastrointestinal Tract", Applied and Environmental Microbiology, 2008, vol. 74, No. 16, pp. 5254.
Maathuis et al., "Survival and Metabolic Activity of the GanedenBC$^{30}$ Strain of *Bacillus coagulans* in a Dynamic in vitro Model of the Stomach and Small Intestine", Beneficial Microbes, 2010, vol. 1, No. 1, pp. 31-36.
International Preliminary Report on Patentability dated Aug. 11, 2015—9 Pages.
Foerster et al., "Response of Bacillus Spores to Combinations of Germinative Compounds", Journal of Bacteriology, 1966, vol. 91, No. 3, pp. 1168-1177.

* cited by examiner

*Primary Examiner* — Renee Claytor
*Assistant Examiner* — Michelle F Paguio Frising
(74) *Attorney, Agent, or Firm* — McCarter & English, LLP

(57) ABSTRACT

In one aspect, the present invention is directed to a dried intimate mixture comprising a bacteria spore and a germinative compound, and methods for preparing the intimate mixture. In another aspect, this invention is directed to a composition comprising such an intimate mixture. The invention also relates to methods for increasing the germination, growth, metabolism, and/or enzyme activity of a bacteria spore comprising preparing an intimate mixture of a bacteria spore and a germinative compound.

15 Claims, No Drawings

DRIED SPORE GERMINATIVE COMPOUND MIXTURES

CROSS REFERENCE TO RELATED APPLICATIONS

This application claims the priority benefit of U.S. Provisional Application Ser. No. 61/849,973 filed Feb. 6, 2013, which is hereby incorporated by reference in its entirety.

FIELD OF THE INVENTION

In one aspect, the present invention is directed to a dried intimate mixture comprising a bacterial spore and a germinative compound, and methods of preparing the mixture. In another aspect, this invention is directed to a composition comprising such a mixture. The invention also relates generally to methods for increasing the germination, growth, metabolism and/or enzyme activity of bacteria spores, comprising preparing a dried intimate mixture comprising a bacterial spore and a germinative compound.

BACKGROUND OF THE INVENTION

The use of spore forming bacteria including certain *Bacillus* strains as probiotics for both humans and animals has become prevalent in recent years. As is noted in Knap et al. (WO 2010/070005) species such as *Bacillus subtilis* and *Bacillus licheniformis* are used as supplements in animal feed in order to promote growth by increasing the digestion and availability of nutrients from animal feed. *Bacillus coagulans* is the active ingredient in commercial probiotic products for human consumption, helping to aid in the digestion of proteins, lactose and fructose.

As is noted in Maathuis et al. (2010, Beneficial Microbes, 1(1): 31-36), such bacteria must be present in the small intestine in their germinated or vegetative form in order to function as probiotics. While such microbes are resistant to both stomach acid and bile salts in their spore form, they are susceptible to such environments in their vegetative states. Thus, if employed in their vegetative state, *Bacillus* strains must be contained within a pharmaceutically-acceptable acid-resistant or "enteric" carrier. See paragraph 7 of Farmer (US Patent Application 2003/0124104).

Unfortunately, it is difficult to formulate *Bacillus* species in their vegetative form such that they will possess an adequate shelf life. As is noted in GanedenBC product literature, traditional vegetative probiotics do not survive high heat and pressure in the manufacturing process, die quickly on the shelf, and are sensitive to stomach acids and bile enzymes in the gut. In contrast, formulations of such species in their spore form are much more suitable for commercial and practical use. Thus, as is noted by Cartman et al. (2008, Applied and Environmental Microbiology, August, p. 5254-5258) "[b]acterial spores are particularly well suited for use as live microbial products as they are metabolically dormant and highly resilient to environmental stress. These intrinsic properties are highly desirable from a commercial perspective and mean that spore-based products have a long shelf life and retain their viability during distribution and storage."

The use of certain compounds, particularly certain L-amino acids, to stimulate the germination of *Bacillus* spores has been reported in the literature. Thus, for example, Foerster et al. (1966, Journal of Bacteriology 91(3): 1168-1177) discloses that the addition of L-alanine to spore suspensions in aqueous solutions will cause the germination of a number of *Bacillus* species. In addition, Maathius et al. cited above, suggests that the *Bacillus coagulans* spores in GanedenBC could be triggered into germination at the beginning of the small intestine by ingesting them together with a diet containing L-alanine, or by including L-alanine with such spores in a powder formulation. However, the approaches suggested by Maathius present several major challenges to establishing a probiotically effective bacterial culture:

1) Although the *Bacillus coagulans* spores employed in GanedenBC are themselves largely resistant to the low pH in the stomach, exposure to such acids could lead to a lag in germination when such spores enter into a more neutral pH. For example, Blocher et al. (1985, Applied and Environmental Microbiology 50(2): 274-279) demonstrated that *B. cereus* spores were inhibited from germinating at pH 4.5 even in the presence of the germinative compounds L-alanine or L-cysteine. Spores sequentially exposed to pH 4.5 buffer followed by pH 7.0 buffer were able to germinate upon exposure to such L-amino acids, but exhibited a lag in commitment to germinate. Any substantial delay in germination is highly undesirable, given the relatively short period of time that the spores may be present in the small intestines before being excreted. This is particularly true in smaller animals such as chicks, which have feed transit times of about 1.5 hours when 1 day old and transit time of less than 2 hours when 7 days old (see B. C. Watson et al. (2006, Poultry Science 85: 493-497), and shrimp, which have a transit time of less than 90 minutes (see Beseres et al., 2005, Journal of Shellfish Research 24(1):301-308). Thus there remains a need for accelerating and increasing germination of bacterial spores under conditions of exposure to low pH, such as those found in the stomach.

2) Diets high in L-alanine may also be high in D-alanine. As noted by Atluri et al. (2006, Journal of Bacteriology 188(1): 28-36), and Blocher et al. (cited above), D-alanine is a powerful inhibitor of *Bacillus* germination. In addition, there can be large amounts of other germination inhibitors (e.g., other D-amino acids, inorganic and organic acids, fatty acids, and bile salts) present in the small intestine which could compete with L-alanine if mixed in a powder foam with *Bacillus* spores. Thus, a need exists to develop a method of improving spore germination in the presence of germination inhibitors that may compete with germinative compounds.

Accordingly, it is an object of this invention to provide a bacterial spore formulation which is capable of providing such benefits.

SUMMARY OF THE INVENTION

It has been surprisingly found that bacterial spore germination, growth, metabolism and enzyme activity are increased through formation of an intimate mixture of the bacterial spore and a germinative compound. Unexpectedly, the intimate mixture also increases germination and growth of the bacteria spores in the presence of germination inhibitors.

In one aspect, the present invention is directed to a dried intimate mixture comprising a bacterial spore and a germinative compound, wherein the bacteria spore and the germinative compound are maintained in proximate position until they reach an environment conducive to germination.

In another aspect, the present invention is directed to a composition comprising a dried intimate mixture comprising a bacterial spore and a germinative compound, wherein the bacteria spore and the germinative compound are maintained in proximate position until they reach an environment conducive to germination.

In a further aspect, the present invention relates to a method for preparing a dried intimate mixture comprising a bacteria spore and a germinative compound, the method comprising:
a) preparing a solution comprising a bacteria spore and a germinative compound; and
b) drying the solution to obtain a dried intimate mixture comprising a bacteria spore and a germinative compound, wherein the bacteria spore and the germinative compound are maintained in proximate position until they reach an environment conducive to germination In a still further aspect, the present invention relates to a method for increasing the germination, growth, metabolism and/or enzyme activity of bacteria spores, comprising:
a) preparing a solution comprising a bacteria spore and a germinative compound; and
b) drying the solution to obtain a dried intimate mixture comprising a bacteria spore and a germinative compound, wherein the bacteria spore and the germinative compound are maintained in proximate position until they reach an environment conducive to germination of the bacterial spores; and
c) exposing the intimate mixture to an environment conducive to germination of the bacteria spores, wherein the germination, growth, metabolism and/or enzyme activity of the bacteria spores in the intimate mixture is increased relative to a corresponding bacteria spore formulation that lacks a germinative compound.

DETAILED DESCRIPTION OF THE INVENTION

The mixtures of this invention are comprised of a bacterial spore and a germinative compound. The bacterial species employed may be any species which forms spores, and is typically one which exhibits desirable probiotic activity in humans or animals. However, bacterial species which have other industrial applications including those useful in agriculture, environmental remediation, composting or methane production, cleaning supplies and the like may also be employed. Such species include spore forming members of the phylum Firmicutes and spore forming members of the phylum Actinobacteria as listed in Bergey's Manual of Systematic Bacteriology, Second Edition (2009), hereby incorporated by reference in its entirety. Members of the phylum Firmicutes include aerobic spore-forming species (generally previously defined as *Bacillus* species) and anaerobic spore-forming species (generally previously defined as *Clostridium* species). Illustrative species of the phylum Firmicutes include *B. alcalophilus, B. alvei, B. amyloliquefaciens, B. aneurinolyticus, B. anthracis, B. aquaemaris, B. atrophaeus, B. boronophilus, B. brevis, B. caldolyyicus, B. centrosporus, B. cereus, B. circulans, B. clausii, B. coagulans, B. firmus, B. flavothermus, B. fusiformis, B. globigii, B. infernus, B larvae, B. laterosporus, B. lentimorbus, B. lentus, B. licheniformis, B. megaterium, B. mesentericus, B. mucilaginosus, B. mycoides, B. natto, B. pantothenicus, B. popilliae, B. polymyxa, B. pseudoanthracis, B. pumilus, B. schlegelii, B. simplex, B. sphaericus, B. sporothermodurans, B. stearothermophilus, B. subtilis, B. thermoglucosidasius, B. thuringiensis, B. vulgatis, B. weihenstephanensis, C. thermocellum, C. ljungdahlii, C. acetobutylicum, C. beijerinckii, C. butyricum, Pasteuria penetrans, Pasteuria thornei*, and *Pasteuria nishizawa*, as well as genetically modified variants of such species. Preferred species include *B. amyloliquefaciens, B. brevis, B. cereus, B. circulans, B. clausii, B. coagulans, B. firmus, B. laterosporus, B. lentus, B. licheniformis B. megaterium, B. polymyxa, B. pumilus, B. simplex, B. sphaericus, B. stearothermophilus, B. subtilis, B. thuringiensis* and *C. butyricum*. Members of the phylum Actinobacteria include *Streptomyces* species, as well as genetically modified variants of such species. Preferred species include *Streptomyces viridochromogenes, Streptomyces griseoviridis, Streptomyces lydicus, Streptomyces plicatus, Streptomyces sindeneusis, Streptomyces rochei, Streptomyces alni, Streptomyces viridis, Streptomyces thermovulgaris, Streptomyces griseus, Streptomyces acidiscabies, Steptomyces aureofaciens, Streptomyces galbus, Streptomyces microflavus*, and *Streptomyces aureofaciens*.

The germinative compound may comprise any compound which is effective to cause germination of the particular spore-forming bacteria species with which it is intimately mixed and which is amenable to processes useful for forming such an intimate mixture such as spray-drying, freeze-drying, air drying or drum drying. Typically, such germinative compounds are L-amino acids including L-alanine, L-valine, L-proline, L-leucine, L-cysteine, L-threonine, L-glutamine, L-asparagine, L-phenylalanine and analogues thereof. Such analogues can be created by one of ordinary skill in the art by making substitutions on or within groups of a base chemistry. Thus, for example, analogues of L-alanine include: L-Leu-L-Ala, L-Ala-L-Leu, L-Pro-LAla, L-Ala-L-Pro, a-L-Glu-L-Ala, L-Ala-L-Glu, L-His-L-Ala, L-Ala-L-His, L-Ala-L-Ala, Gly-L-Ala, L-Ala-Gly, N42-methylsulphonyl)ethyloxycarbonyl-L-alanine dicyclohexylammonium salt (N-MSOC-L-Ala), N-t-butoxycarbonyl-L-alanine (N-t-BOC-L-Ala), N-acetyl-L-alanine (N-Ac-L-Ala), N-2,4-dinitrophenyl-L-alanine (N-DNP-L-Ala), Ncarbobenzoxy-L-alanine (N-CBZ-L-Ala), 5-dimethylamino-1-naphthalenesulphonyl-L-alanine cyclohexylamine salt (N-dansyl-L-Ala), N-benzoyl-L-alanine (N-Bz-L-Ala), L-alanine methyl ester hydrochloride, L-alanine ethyl ester hydrochloride, L-alanine t-butyl ester hydrochloride, L-alanine benzyl ester hydrochloride, L-alaninamide, L-alanine p-nitroanilide hydrochloride and L-alaminol. In one embodiment, the germinative compound is an amino acid selected from the group consisting of L-alanine, L-valine, L-proline, L-leucine, L-cysteine, L-threonine, L-glutamine, L-asparagine, and L-phenylalanine. Preferably, such germinative compound is L-alanine.

Such amino acids can be employed as individual compounds, or in the form of polypeptides. In one embodiment the polypeptides are protein hydrolysates, for example casein hydrolysate. Useful polypeptides will typically comprise at least fifty percent amino acids which will function as germinants, such as L-alanine, L-valine, L-proline, L-leucine, L-cysteine, L-threonine, L-glutamine, L-asparagine, and L-phenylalanine, such percentages being based upon the number of amino acids in the polypeptide.

In a preferred embodiment, the germinative compound is selected from the group consisting of L-amino acids, proteins, sugars, and salts. Particularly preferred bacterial spore/germinative compound combinations include L-alanine+*Bacillus subtilis*, L-alanine+*Bacillus licheniformis*, L-alanine+*Bacillus pumilus*, L-alanine+*Bacillus amyloliquefaciens*, L-alanine+*Bacillus coagulans*, L-alanine+*Bacillus cereus*, L-alanine+*Bacillus clausii*, L-alanine+*Clostridium butyricum*

L-valine+*Bacillus subtilis*, L-valine+*Bacillus licheniformis*, L-valine+*Bacillus pumilus*, L-valine+*Bacillus amylolique-*

*faciens*, L-valine+*Bacillus coagulans*, L-valine+*Bacillus cereus*, L-valine+*Bacillus clausii*, L-valine+*Clostridium butyricum*

L-alanine+glucose+fructose+potassium ions (GFK)+*Bacillus subtilis*, L-alanine+glucose+fructose+potassium ions (GFK)+*Bacillus licheniformis*, L-alanine+glucose+fructose+potassium ions (GFK)+*Bacillus pumilus*, L-alanine+glucose+fructose+potassium ions (GFK)+*Bacillus amyloliquefaciens*, L-alanine+glucose+fructose+potassium ions (GFK)+*Bacillus coagulans*, L-alanine+glucose+fructose+potassium ions (GFK)+*Bacillus cereus*, L-alanine+glucose+fructose+potassium ions (GFK)+*Bacillus clausii*, L-alanine+glucose+fructose+potassium ions (GFK)+*Clostridium butyricum*

L-asparagine+glucose+fructose+potassium ions (GFK)+*Bacillus subtilis*, L-asparagine+glucose+fructose+potassium ions (GFK)+*Bacillus licheniformis*, L-asparagine+glucose+fructose+potassium ions (GFK)+*Bacillus pumilus*, L-asparagine+glucose+fructose+potassium ions (GFK)+*Bacillus amyloliquefaciens*, L-asparagine+glucose+fructose+potassium ions (GFK)+*Bacillus coagulans*, L-asparagine+glucose+fructose+potassium ions (GFK)+*Bacillus cereus*, L-asparagine+glucose+fructose+potassium ions (GFK)+*Bacillus clausii*, L-asparagine+glucose+fructose+potassium ions (GFK)+*Clostridium butyricum*

L-alanine+inosine+*Bacillus subtilis*, L-alanine+inosine+*Bacillus licheniformis*, L-alanine+inosine+*Bacillus pumilus*, L-alanine+inosine+*Bacillus amyloliquefaciens*, L-alanine+inosine+*Bacillus coagulans*, L-alanine+inosine+*Bacillus cereus*, L-alanine+inosine+*Bacillus clausii*, L-alanine+inosine+*Clostridium butyricum*, L-proline+glucose+*Bacillus megaterium*, L-proline+*Bacillus megaterium*, and L-lactate+*Clostridium butyricum*.

In certain embodiments, preferred mixtures of the present invention include those wherein the spore is selected from the group consisting of *B. subtilis*, *B. amyloliquefaciens*, *B. licheniformis*, *B. megaterium*, and *B. pumilus*; and the germinative compound is selected from the group consisting of L-alanine, L-valine, and L-asparagine.

The germinative compound is present in an amount sufficient to cause the bacterial spore employed to germinate. Although this can be readily determined for any particular bacterial spore/germinative compound mixture by routine experimentation, such germinative compounds are typically formulated, prior to drying, at concentrations of from 0.0001 mg/mL to 170 mg/mL. In some embodiments, the germinative compounds are formulated, prior to drying, at concentrations of 0.0003 mg/mL to 170 mg/mL, 0.0003 mg/mL to 30 mg/mL, 0.001 mg/mL to 100 mg/mL, or 0.001 mg/mL to 10 mg/mL. In a preferred embodiment, the germinative compound is formulated, prior to drying, at concentrations of from 0.001 mg/mL to 1 mg/mL.

As is employed herein, the term "intimate mixture" refers to a mixture in which the spores and germinative compounds are maintained in proximate position until they reach an environment conducive to germination.

Such an intimate mixture can be achieved employing processes such as spray-drying, freeze-drying, air drying or drum drying. In a preferred embodiment, the intimate mixture is produced by spray-drying or freeze-drying. When forming such intimate mixtures, it is important that the spore and germinative compound are not mixed together under conditions which would allow the germinative compound to cause the spore to germinate, as this could cause premature germination with an adverse effect upon the storage life of the mixture. This can be avoided by employing separate streams in a spray-dryer, either by using two nozzles or a single nozzle which permits the simultaneous spraying of two separate streams; or by freeze-drying under conditions (for example temperatures) which are not conducive to germination. Premature germination may also be avoided by introducing the spore mass to a solution containing the germinative compound immediately prior to drying.

In a preferred embodiment, the germinative compound is adsorbed to or absorbed by the bacteria spore in the intimate mixture. In a further embodiment, the bacteria spore and germinative compound are finely dispersed throughout the intimate mixture. In a still further embodiment, the bacteria spore and germinative compound are microscopically dispersed throughout the intimate mixture, such that individual particles consisting essentially of bacteria spores and individual particles consisting essentially of germinative compounds are not visible to the naked eye.

In one embodiment the intimate mixture is prepared by combining the bacteria spore and germinative compound in a solution prior to drying. Preferably, the bacteria spore and germinative compound are combined in a solution immediately prior to drying.

Although not wishing to be held to any theory, it is believed that the formation of an intimate mixture places the germinative compound in a proximate position where it can more preferably bind to the germination initiator sites of the spore when the mixture reaches an appropriate environment for germination. Such proximate position permits the germinative compound to outcompete germination interfering compounds (such as D-amino acids) which may be present, with the result that a higher percentage of spores will be germinated. Due to the logarithmic growth of bacteria once they enter the vegetative stage; such an increased percentage can quickly result in a several log increase in culture formation.

The present invention also relates to compositions comprising an intimate mixture comprising (a) a bacterial spore and (b) a germinative compound, wherein the spore and germinative compound are maintained in an inactive form such that the germinative compound will not induce germination of the spore until such composition is subjected to an activation environment.

As is employed herein, the term "activation environment" refers to an environment which permits the germinative compound and the spore to interact, such that the spore is induced to enter into a vegetative state. Such an activation environment may involve a combination of factors such as temperature, moisture, pH or salinity.

The formation of an intimate mixture of a germinative compound and a bacteria spore may enhance the utility of the bacteria spore by increasing one or more traits of interest of the bacteria spore, including but not limited to germination, growth, metabolism, enzyme activity and tolerance to environmental stresses such as low pH, high salt concentration, and exposure to toxic metals. In some embodiments, the intimate mixture increases the trait of interest by at least 5, 10, 20, 30, 40, 50, 60, 70, 80, 90, 100, 200, 300, 400 or 500% relative to a corresponding bacteria spore formulation that lacks a germinative compound.

In order to further enhance germination, it is preferred that the spore be shocked prior to the formation of the intimate mixture. Spores may be shocked in a variety of standard methods, e.g., osmotic shock, heat shock, pressure shock, deprivation of nutrients, and/or exposure to certain acids. Heat shock involves heating the spores for a sufficient period of time at a temperature sufficient to induce the production of heat shock proteins. Atluri et al., cited above, describes one such heat shock treatment for *Bacillus subtilis*.

The compositions of this invention comprise an intimate mixture comprising a bacteria spore and a germinative compound. Such compositions may further comprise additional components, including co-germinants, nutrients, and formulation aids (for example surfactants and/or enteric coatings) depending upon their intended use.

Co-germinants which may be employed include purine nucleosides such as inosine or adenosine, salts, sugars (such as glucose and fructose), and the like; all of which are well known to those of skill in the art.

Nutrients, including dextrose, starches, and micronutrients which will aid in the multiplication of bacterial colonies once the spores have germinated may also be included.

When the composition is intended for use as a probiotic, the use of an enteric coating is preferably employed in order to avoid the lag in spore germination associated with the exposure of spores to low pH environments. Such enteric coating is designed to resist solution in the stomach and to dissolve in the neutral or alkaline intestinal fluid. Such coating may be pH-sensitive, e.g., not dissolving in an acidic environment as is encountered in the stomach but dissolving in a neutral environment as is encountered in the small intestine. Alternatively, the enteric coating may dissolve when exposed to specific metabolic event such as an encounter with a digestive enzyme that is found in the small intestine. For example, the coating is digested by a pancreatic enzyme such as trypsin, chymotrypsin, or a pancreatic lipase. Digestion or dissolution of the coating allows the Bacillus spore/germinative compound to enter into an environment conducive to the germination of the spores.

Enteric coating materials which may be employed are known in the art and include alginates, malic acid-propane 1,2-diol; cellulose derivatives, e.g., cellulose acetate phthalate or hydroxypropyl methylcellulose phthalate (HPMCP); cellulose acetate phthalate, polyvinyl acetate phthalate, hydroxypropylmethylcellulose phthalate and anionic polymers of methacrylic acid and methyl methacrylate; and a water emulsion of ethylacrylate methylacrylic acid copolymer, or hydroxypropyl methyl cellulose acetate succinate (HPMAS).

When employed in agricultural or industrial uses, such compositions may further comprise standard formulation aids such as surfactants, emulsifiers, other active ingredients, etc. so long as other components do not interfere with germination or adversely affect the viability of the germinated spores. For example, phenolic compounds which are not otherwise particularly sporocidal are known to inhibit germination at concentrations as low as 0.2% (phenol), 0.08% (cresol), and 0.02% (chlorocresol) (wt./vol). Other compounds which may inhibit germination are also well known in the art. See, for example, A. D. Russell, Bacterial Spores and Chemical Sporicidal Agents, *CLINICAL MICROBIOLOGY REVIEWS*, April 1990, p. 99-119.

The invention also provides a method for preparing a dried intimate mixture comprising a bacteria spore and a germinative compound, the method comprising:
a) preparing a solution comprising a bacteria spore and a germinative compound; and
b) drying the solution to obtain a dried intimate mixture comprising a bacteria spore and a germinative compound, wherein the bacteria spore and the germinative compound are maintained in proximate position until they reach an environment conducive to germination.

In a preferred embodiment the drying in the aforementioned method is spray-drying, freeze-drying, air drying or drum drying. In another preferred embodiment, the spore in the aforementioned method is selected from the group consisting of *B. alcalophilus, B. alvei, B. amyloliquefaciens, B. aneurinolyticus, B. anthracia, B. aquaemaris, B. atrophaeus, B. boronophilus, B. brevis, B. caldolyyicus, B. centrosporus, B. cereus, B. circulans, B. clausii, B. coagulans, B. firmus, B. flavothermus, B. fusiformis, B. globigii, B. infernus, B larvae, B. laterosporus, B. lentus, B. lentimorbus, B. licheniformis, B. megaterium, B. mesentericus, B. mucilaginosus, B. mycoides, B. natto, B. pantothenicus, B. popilliae, B. polymyxa, B. pseudoanthracis, B. pumilus, B. schlegelii, B. simplex, B. sphaericus, B. sporothermodurans, B. stearothermophilus, B. subtilis, B. thermoglucosidasius, B. thuringiensis, B. vulgatis, B. weihenstephanensis, C. thermocellum, C. ljungdahlii, C. acetobutylicum, C. beijerinckii, C. butyricum, Pasteuria penetrans, Pasteuria thornei, Pasteuria nishizawae*, and *Streptomyces* spp.

In a further preferred embodiment, the spore in the aforementioned method is selected from the group consisting of *B. subtilis, B. amyloliquefaciens, B. licheniformis, B. megaterium*, and *B. pumilus*; and the germinative compound in the aforementioned method is selected from the group consisting of L-alanine, L-valine, and L-asparagine.

The germinative compound in the aforementioned method may be formulated, prior to drying, at concentrations from 0.0001 mg/ml to 170 mg/ml. In some embodiments of the aforementioned method, the germinative compounds are formulated, prior to drying, at concentrations of 0.0003 mg/mL to 170 mg/mL, 0.0003 mg/mL to 30 mg/mL, 0.001 mg/mL to 100 mg/mL, or 0.001 mg/mL to 10 mg/mL. In a preferred embodiment of the aforementioned method, the germinative compound is formulated, prior to drying, at concentrations of from 0.001 mg/mL to 1 mg/mL. In certain embodiments, the germinative compound in the aforementioned method is a polypeptide. In a preferred embodiment of the aforementioned method, the spore has been shocked.

The invention also provides a dried intimate mixture produced by the aforementioned methods.

In another aspect, the invention provides a method for increasing the germination, growth, metabolism and/or enzyme activity of bacteria spores, comprising:
a) preparing a solution comprising a bacteria spore and a germinative compound; and
b) drying the solution to obtain a dried intimate mixture comprising a bacteria spore and a germinative compound, wherein the bacteria spore and the germinative compound are maintained in proximate position until they reach an environment conducive to germination of the bacterial spores; and
c) exposing the intimate mixture to an environment conducive to germination of the bacteria spores, wherein the germination, growth, metabolism and/or enzyme activity of the bacteria spores in the intimate mixture is increased relative to a corresponding bacteria spore formulation that lacks a germinative compound.

In some embodiments of the aforementioned method, the intimate mixture increases the trait of interest by at least 5, 10, 20, 30, 40, 50, 60, 70, 80, 90, 100, 200, 300, 400 or 500% relative to a corresponding bacteria spore formulation that lacks a germinative compound.

In a preferred embodiment of the aforementioned method, the percent germination, growth, metabolism and/or enzyme activity of bacteria spores in the intimate mixture is increased by at least 10% relative to the corresponding bacteria spore formulation that lacks a germinative compound. In a further preferred embodiment of the aforementioned method, the drying is spray-drying, freeze-drying, air drying or drum drying.

In certain embodiments, the spore in the aforementioned method is selected from the group consisting of *B. alcalophilus, B. alvei, B. amyloliquefaciens, B. aneurinolyticus, B. anthracia, B. aquaemaris, B. atrophaeus, B. boronophilus, B. brevis, B. caldolyyicus, B. centrosporus, B. cereus, B. circulans, B. clausii, B. coagulans, B. firmus, B. flavothermus, B. fusiformis, B. globigii, B. infernus, B larvae, B. laterosporus, B. lentus, B. lentimorbus, B. licheniformis, B. megaterium, B. mesentericus, B. mucilaginosus, B. mycoides, B. natto, B. pantothenicus, B. popilliae, B. polymyxa, B. pseudoanthracis, B. pumilus, B. schlegelii, B. simplex, B. sphaericus, B. sporothermodurans, B. stearothermophilus, B. subtilis, B. thermoglucosidasius, B.* thuringiensis, B. vulgatis, B. weihenstephanensis, C. thermocellum, C. ljungdahlii, C. acetobutylicum, C. beijerinckii, C. butyricum, Pasteuria penetrans, Pasteuria thornei, Pasteuria nishizawae, and Streptomyces spp. In a preferred embodiment, the spore is selected from the group consisting of B. subtilis, B. amyloliquefaciens, B. licheniformis, B. megaterium, and B. pumilus; and the germinative compound is selected from the group consisting of L-alanine, L-valine, and L-asparagine.

In some embodiments of the aforementioned method, the germinative compound is a polypeptide. In a preferred embodiment the germinative compound in the aforementioned method is formulated, prior to drying, at concentrations from 0.0001 mg/ml to 170 mg/ml. In some embodiments of the aforementioned method, the germinative compounds are formulated, prior to drying, at concentrations of 0.0003 mg/mL to 170 mg/mL, 0.0003 mg/mL to 30 mg/mL, 0.001 mg/mL to 100 mg/mL, or 0.001 mg/mL to 10 mg/mL. In a preferred embodiment of the aforementioned method, the germinative compound is formulated, prior to drying, at concentrations of from 0.001 mg/mL to 1 mg/mL. In a further preferred embodiment of the aforementioned method, the spore has been shocked.

EXAMPLES

The following examples are intended to further illustrate the invention, but are not intended to limit the invention in any manner whatsoever.

In the following Examples, the terms "GOSD" and "GO+" refer to compositions in which a germinative optimizer (L-alanine unless specified otherwise) was spray dried with the particular Bacillus species indicated. Spores of Bacillus species were spray dried with L-alanine being introduced to the spore mass immediately prior to spray drying as a solution containing 0.044 grams of alanine per milliliter of distilled water.

The term "GO−" refers to compositions wherein the Bacillus species was similarly spray dried without a germinative compound being present.

Further, the following method was employed to determining spore germination in the following Examples unless otherwise indicated. When spores are placed in nutrient solutions and begin to germinate they release dipicolinic acid and ions which results in darkening. This indicator of germination results in a decrease in the optical extinction of visible light by a spore suspension. The rate of germination was therefore determined by counting the proportion of phase dark/bright spores, and monitoring the decrease in optical density at 600 nm (O.D. 600) of germinating spore suspensions under a u.v.-visible spectrophotometer. This is then converted to percent germination.

Example 1

Increased Germination of B. Subtilis ENV 923 in an Intimate Mixture with L-Alanine In order to compare the germination rate of the spores of intimate mixtures this invention with that of spores conventionally mixed with a germinant, the following treatments were performed:

A. Formation of an Intimate Mixture: Spores of B. subtilis ENV 923 were spray dried with L-alanine being introduced to the spore mass immediately prior to spray drying as a solution containing 0.044 grams of alanine per milliliter of distilled water. The intimate mixture produced was germinated by subsequent introduction in a solution consisting of 0.01 M phosphate buffer in distilled water with resultant pH 7 and calibrated to a starting O.D. 600 of 0.6.

B. Conventional Mixing of Spores with a Germinant: Spores of B. subtilis ENV 923 were spray dried and subsequently introduced into a solution consisting of 0.01 M phosphate buffer in distilled water with resultant pH 7. Spores were added to the buffer solution to calibrate to a starting O.D. 600 of 0.6. Alanine was added to the solution at a concentration of 0.0001 grams of alanine per milliliter of solution.

C. Germination of Spores Alone: Spores of B. subtilis ENV 923 were spray dried and subsequently introduced into a solution consisting of 0.01 M phosphate buffer in distilled water with resultant pH 7 and calibrated to a starting O.D. 600 of 0.6.

Two replications of each such treatment were performed. Table 1 below shows the average results of such treatments affecting the germination of B. subtilis ENV 923 as measured by a percent drop in optical density. A drop in optical density indicates progression of germination. Optical density (OD) was measured at 600 nm wavelength with a Jenway Model 6320D Visible Range Spectrophotometer. L-alanine utilized was 99% purity and sourced from Alfa Aeser; Heysham, Lancashire, United Kingdom.

TABLE 1

Percent reduction from OD (600 nm) baseline over time.

| Sample time (minutes) | 0 | 5 | 10 | 15 | 20 |
|---|---|---|---|---|---|
| Intimate Mixture | 0% | 2.7% | 17.7% | 34.3% | 41.2% |
| Conventional Mixing | 0% | 0.5% | 18.8% | 31.9% | 33.7% |
| Spores Alone | 0% | 1.3% | 3.2% | 4.1% | 7.5% |

The above results show that the spores in the intimate mixtures of this invention germinate more rapidly than do spores which are not intimately mixed with the same germinant. Spore mixed with germinant exhibited much greater germination than spores alone.

Example 2

Increased Germination of Bacillus subtilis Strain ENV923 Treated with GOSD

Bacillus subtilis spores were treated with GOSD via spray drying spores in the presence of a solution of L-alanine and germination levels were determined via Optical Density (OD) readings.

0.01 M Potassium Phosphate Buffer, pH 7

The 0.01M Potassium Phosphate buffer was prepared using 1M $K_2HPO_4$ (87.09 g dissolved in 0.5 L distilled water) and 1M $KH_2PO_4$ (68.045 g dissolved in 0.5 L distilled water) solutions. Combining 61.5 ml of 1M $K_2HPO_4$ with 38.5 ml 1 M $KH_2PO_4$ and diluting to 1000 ml with distilled water 0.1M Potassium Phosphate buffer at pH7.0 was made. Further diluting the 0.1M Potassium Phosphate buffer with distilled water at the ration 1:10, the 0.01M Potassium Phosphate buffer, pH 7.0 was obtained. The buffer was sterilized by autoclaving at 121° C. for sixty (60) minutes.

Bacillus subtilis spore suspensions were prepared at the concentration $1.7 \times 10^8$ cfu/ml in 0.01 M Potassium Phosphate buffer, pH 7.0, incubated in the preheated 37° C. water bath, and evaluated for percent of germination in 5 minute intervals over a 45 minute period.

TABLE 2

% Germination of *Bacillus subtilis* ENV923
at 37° C. with and without GOSD treatment

| Minutes | 0 | 5 | 10 | 15 | 20 | 25 | 30 | 35 | 40 | 45 |
|---|---|---|---|---|---|---|---|---|---|---|
| *B. subtilis* GOSD | 0 | 13% | 45% | 63% | 64% | 75% | 76% | 80% | 81% | 83% |
| *B. subtilis* Control | 0 | 7% | 9% | 10% | 11% | 14% | 14% | 16% | 18% | 19% |

Conclusion: GOSD treatment significantly enhanced the percent germination and speed of germination of *Bacillus subtilis* spores.

Example 3

Increased Germination of *Bacillus licheniformis* Strain ENV100 Treated with GOSD

*Bacillus licheniformis* spores were treated with GOSD via spray drying spores in the presence of 0.044 grams of L-alanine per mL of distilled water as described in Example 1. Germination levels were determined via Optical Density (OD) readings as described above using 0.01 M Potassium Phosphate buffer, pH 7.0 for spore suspension preparation.

*Bacillus licheniformis* spore suspensions were prepared at the concentration $1.29 \times 10^8$ cfu/ml in 0.01 M Potassium Phosphate buffer, pH 7.0, incubated in the preheated 37° C. water bath, and evaluated for percent of germination in five (5) minute intervals over a forty five (45) minute period.

TABLE 3

% Germination of *Bacillus licheniformis* treated and non-treated spore suspensions

| Minutes | 0 | 5 | 10 | 15 | 20 | 25 | 30 | 35 | 40 | 45 |
|---|---|---|---|---|---|---|---|---|---|---|
| *B. licheniformis*, control | 0 | 1% | 5% | 3% | 10% | 11% | 10% | 10% | 10% | 10% |
| *B. licheniformis*, GOSD | 0 | 4% | 5% | 39% | 60% | 81% | 85% | 88% | 91% | 91% |

Conclusion: GOSD treatment significantly enhanced percent germination and speed of germination of *Bacillus licheniformis* spores.

Example 4

Increased Germination at Various pH Levels for *Bacillus subtilis* Strain ENV923 Treated with GOSD

*Bacillus subtilis* strain ENV923 GO+ and GO− spores were prepared as described above and re-suspended in 0.01 M Potassium Phosphate buffer at various pH levels. $OD_{600}$ measurements were performed as described above.

0.01M Potassium Phosphate Buffers at pH 3.0-7.0

0.01M Potassium Phosphate buffer, pH 7.0 buffer was prepared as described in Example 1.

To prepare 0.01M Potassium Phosphate buffers with pH range from 3.0 to 6.0 as base buffer was used 0.1 M Potassium Phosphate buffer, pH 6.0 made by mixing 13.2 ml of 1M $K_2HPO_4$ and 86.8 ml of 1M $KH_2PO_4$ solutions (described in Example 1) and bringing the volume to 1 L with distilled water.

To obtain 0.01 M Potassium Phosphate buffers with pH 5.0 to pH 3.0, 0.1 M Potassium Phosphate buffer, pH 6.0 was diluted with distilled water, pH of buffers was lowered to pH 5.0, pH 4.0 and pH 3.0 using 1M $H_3PO_4$ and final volume brought up with distilled water keeping ratio of 0.1 M buffer to distilled water 1:10.

Prepared buffers were stored at 4° C. and prior to each experiment pH of buffers was re-adjusted using 1 M NaOH or 1 M $H_3PO_4$.

TABLE 4

Germination results with GOSD (GO+) and without GOSD (GO−) at various pH levels, table shows percent germination measured at 5 minute intervals.

| Minutes | 0 | 5 | 10 | 15 | 20 | 25 | 30 | 35 | 40 | 45 |
|---|---|---|---|---|---|---|---|---|---|---|
| GO+ pH 7 | 0 | 8% | 48% | 69% | 80% | 84% | 88% | 90% | 91% | 92% |
| GO− pH 7 | 0 | 3% | 3% | 8% | 10% | 11% | 13% | 14% | 16% | 16% |

TABLE 4-continued

Germination results with GOSD (GO+)and without GOSD (GO−) at various pH levels, table shows percent germination measured at 5 minute intervals.

| Minutes | 0 | 5 | 10 | 15 | 20 | 25 | 30 | 35 | 40 | 45 |
|---|---|---|---|---|---|---|---|---|---|---|
| GO+ pH 6 | 0 | 4% | 40% | 58% | 69% | 75% | 77% | 78% | 81% | 82% |
| GO− pH 6 | 0 | 1% | 4% | 5% | 9% | 8% | 11% | 13% | 12% | 12% |
| GO+ pH 5 | 0 | 7% | 24% | 34% | 39% | 41% | 43% | 45% | 46% | 46% |
| GO− pH 5 | 0 | 4% | 4% | 5% | 5% | 6% | 6% | 7% | 7% | 7% |
| GO+ pH 4 | 0 | 5% | 23% | 28% | 30% | 31% | 33% | 32% | 33% | 34% |
| GO− pH 4 | 0 | 3% | 4% | 5% | 4% | 4% | 5% | 3% | 4% | 4% |
| GO+ pH 3.5 | 0 | 5% | 11% | 16% | 18% | 18% | 18% | 18% | 20% | 20% |
| GO− pH 3.5 | 0 | 2% | 1% | 1% | 1% | 1% | 1% | 2% | 0% | 1% |
| GO+ pH 3 | 0 | 11% | 16% | 19% | 19% | 22% | 21% | 22% | 21% | 22% |
| GO− pH 3 | 0 | 4% | 4% | 4% | 5% | 2% | 3% | 4% | 2% | 4% |

Conclusion: Treatment with GOSD enables *Bacillus subtilis* spores to germinate faster and overcome the effects of lower pH levels.

Example 5

Increased Germination of *Bacillus subtilis* Strain ENV923 Treated with GOSD. Spore Germination Response as Affected by Various Temperature Levels. Table Shows Percent Germination Measured at 10 Minute Intervals

*Bacillus subtilis* strain ENV 923 GOSD and Control spores were prepared as described above. Germination of spores was tested via Optical Density (OD) measurements as described above. Spore suspensions for $OD_{600}$ measurements were prepared and cooled to 4° C. in 0.01 M Potassium Phosphate buffer, pH 7.0 (Phosphate buffer, pH 7.0 preparation) at the concentration $1.7 \times 10^8$ cfu/ml. For each spore suspension 3 culture tubes filled to 3 ml volume were prepared. Following agitation and initial $OD_{600}$ measurement the tubes were incubated in water baths preheated to 25° C., 30° C. and 37° C. for 120 min. At 10 min intervals tubes were agitated and $OD_{600}$ measurements taken.

TABLE 5

Percent germination of *Bacillus subtilis* with GO− and GO+ at 37° C., 30° C. and 25° C.

| Minutes | 0 | 10 | 20 | 30 | 40 | 50 | 60 | 70 | 80 | 90 | 100 | 110 | 120 |
|---|---|---|---|---|---|---|---|---|---|---|---|---|---|
| GO+, 37° C. | 0 | 36% | 58% | 63% | 68% | 70% | 70% | 71% | 70% | 70% | 70% | 70% | 70% |
| GO+, 30° C. | 0 | 12% | 32% | 45% | 52% | 55% | 58% | 59% | 58% | 60% | 60% | 60% | 60% |
| GO+, 25° C. | 0 | 1% | 9% | 16% | 23% | 28% | 32% | 33% | 35% | 37% | 36% | 35% | 35% |
| GO−, 37° C. | 0 | 1% | 4% | 6% | 7% | 9% | 9% | 9% | 9% | 9% | 9% | 9% | 9% |
| GO−, 30° C. | 0 | 0% | 2% | 3% | 4% | 6% | 6% | 7% | 7% | 8% | 9% | 8% | 7% |
| GO−, 25° C. | 0 | 0% | 2% | 3% | 4% | 5% | 7% | 8% | 8% | 9% | 10% | 10% | 10% |

Conclusion: Treatment with GOSD (GO+) enables *Bacillus subtilis* spores to germinate faster and overcome the effects of lower temperature regimes.

Example 6

Percent Germination of *Bacillus licheniformis* with and without GOSD in the Presence of Different Molar Solutions of NaCl Medium:
The medium was a dilute Tryptic Soy Broth (mTSB) (BD, 211822). The medium was prepared by suspending 50 mg of Tryptic Soy Broth powder in 1 L water with heat and agitation until completely dissolved. It was then aliquoted into bottles and autoclaved for 30 minutes at 121° C. Based on the manufacture's reported powder contents, the mTSB media contained per liter:
Pancreatic Digest of Casein: 28.3 mg
Papic Digest of Soybean: 5.0 mg
Dextrose: 4.2 mg
Sodium Chloride: 8.3 mg
Dipotassium Phosphate: 4.2 mg Sodium chloride (Amresco X190) was added to induce osmotic stress where appropriate such that the final concentrations were 0.5 M or 1.5 M (29.22 g/L and 87.66 g/L respectively) before the media was heated and autoclaved.

Spore Suspensions:
Spore powders of *Bacillus licheniformis* strain ENV 100 treated or not treated with GOSD were suspended in sterile water with 0.1% Octosol SLS (FT-SLS-246DRUM, Tiarco Chemical, Dalton, Ga.) within a sterile blender jar. Spores were suspended by blending for 5 second intervals for a total of at least 15 seconds or until the spores were completely suspended visually. This was performed such that the final concentration in the blender jar was $1 \times 10^{10}$ cfu/ml. From this spore suspension, 250 µl was transferred to tubes containing 4.75 ml mTSB to give a final concentration of $5 \times 10^8$ cfu/ml. These concentrations are determined by optimizations performed on each batch of spores to achieve a starting OD600 of approximately 0.6.

OD Germination Assay:
Tubes containing the suspended spores were immediately vortexed, measured at OD600 for time point zero, and incubated in a 37° C. water bath. At respective time intervals, the time was recorded, tubes were removed, vortexed, measured at OD600 and returned to the water bath. The percent decrease in OD600 was determined by subtracting the measured value from the zero time point, divided by the zero time point and multiplied by 100%. Full germination was previously documented to correspond to a percent OD600 decrease of 60%. Therefore Percent Germination was determined by multiplying the percent OD600 decrease by 1.67.

TABLE 6

% Germination of *Bacillus licheniformis* spores over one hour with GOSD (GO+) and without (GO−) in the presence of 0, .5 Molar and 1.5 Molar solutions of NaCl.

| Time | GO+ 0M | GO− 0M | GO+ 0.5M | GO− 0.5M | GO+ 1.5M | GO− 1.5M |
|---|---|---|---|---|---|---|
| 0:00 | 0 | 0 | 0 | 0 | 0 | 0 |
| 0:11 | 7% | 0% | 29% | 1% | 15% | 2% |
| 0:16 | 23% | 0% | 49% | 0% | 30% | 0% |
| 0:22 | 44% | 3% | 61% | 0% | 44% | 0% |
| 0:27 | 53% | 0% | 67% | 0% | 48% | 0% |
| 0:32 | 59% | 0% | 70% | 1% | 53% | 0% |
| 0:38 | 64% | 0% | 74% | 1% | 56% | 0% |
| 0:43 | 68% | 0% | 75% | 0% | 58% | 0% |
| 0:49 | 71% | 0% | 77% | 0% | 61% | 0% |
| 0:55 | 72% | 0% | 77% | 2% | 63% | 0% |
| 1:01 | 75% | 0% | 78% | 2% | 66% | 0% |

Conclusion: Treatment with GOSD enables *Bacillus licheniformis* spores to germinate faster and overcome the osmotic stress effects of various salt (NaCl) levels.

Example 7

Percent Germination of *Bacillus licheniformis* with and without GOSD in the Presence of Different Part Per Million Solutions of Copper Medium:

mTSB medium was prepared as above, but supplemented with NaCl to a final concentration of 50 mM to create an osmotically balanced media. A $1\times10^5$ ppm Copper (II) nitrate hemi(pentahydrate) (Alfa Aesar 12523) stock solution was made by suspending 2 g into 20 ml water, and 0.22 μm filtering. This was added to mTSB aliquots to achieve 0, 50, 100, and 200 ppm final concentrations.

Spore Suspensions:

Spore powders of *Bacillus licheniformis* strain ENV 100 treated or not treated with GOSD were suspended in sterile water with 0.1% Octosol SLS (FT-SLS-246DRUM, Tiarco Chemical, Dalton, Ga.) within a sterile blender jar. Spores were suspended by blending for 5 second intervals for a total of at least 15 seconds or until the spores were completely suspended visually. This was performed such that the final concentration in the blender jar was $2\times10^9$ cfu/ml. From this spore suspension, 250 μl was transferred to tubes containing 4.75 ml mTSB to give a final concentration of $1\times10^8$ cfu/ml. These concentrations are determined by optimizations performed on each batch of spores to achieve a starting OD600 of approximately 0.6.

OD Germination Assay: Performed and calculated as indicated in Example 6.

TABLE 7

Percent germination of *Bacillus licheniformis* spores over one hour with GOSD (GO+) and without (GO−) in the presence of 0, 50 ppm, 100 ppm and 200 ppm solutions of Copper ions.

| Time | GO+ 0 ppm | GO− 0 ppm | GO+ 50 ppm | GO− 50 ppm | GO+ 100 ppm | GO− 100 ppm | GO+ 200 ppm | GO− 200 ppm |
|---|---|---|---|---|---|---|---|---|
| 0:00 | 0.00 | 0.00 | 0.00 | 0.00 | 0.00 | 0.00 | 0.00 | 0.00 |
| 0:05 | 3.1% | 0.6% | 7.7% | 1.5% | 7.8% | 1.4% | 5.0% | 2.8% |
| 0:11 | 19.8% | 1.1% | 14.3% | 2.0% | 12.5% | 1.9% | 9.0% | 4.6% |
| 0:16 | 34.1% | 2.2% | 25.2% | 2.0% | 16.7% | 3.3% | 11.5% | 4.6% |
| 0:21 | 40.9% | 4.4% | 30.7% | 1.5% | 19.3% | 5.1% | 14.0% | 4.6% |
| 0:26 | 47.7% | 4.4% | 34.0% | 2.0% | 18.2% | 5.1% | 15.0% | 6.5% |
| 0:31 | 50.2% | 4.4% | 38.4% | 1.5% | 21.9% | 5.6% | 15.0% | 5.6% |
| 0:36 | 50.8% | 4.4% | 38.9% | 0.5% | 20.8% | 6.1% | 17.0% | 6.0% |
| 0:41 | 52.0% | 3.3% | 40.6% | 1.5% | 21.4% | 6.5% | 18.0% | 5.6% |
| 0:47 | 55.8% | 3.9% | 45.0% | 3.0% | 26.0% | 7.5% | 20.0% | 6.0% |
| 0:53 | 57.0% | 2.8% | 44.4% | 2.5% | 25.5% | 8.4% | 19.5% | 6.0% |
| 0:58 | 57.6% | 3.9% | 45.5% | 3.0% | 25.0% | 8.4% | 20.5% | 6.9% |
| 1:04 | 60.1% | 4.4% | 45.0% | 1.0% | 24.5% | 8.4% | 21.0% | 4.6% |

Conclusion: Treatment with GOSD enables *Bacillus licheniformis* spores to germinate faster and overcome the stress effects of various levels of Copper ions.

Example 8

Percent Germination of *Bacillus licheniformis* with and without GOSD in the Presence of Different Part Per Million Solutions of Aluminum Medium:

mTSB medium was prepared as above, but supplemented with NaCl to a final concentration of 50 mM to create an osmotically balanced media. A 1000 ppm $Al^{3+}$ stock solution was made by suspending 0.62 g of $Al_2(SO_4)_3 \cdot 14\,H_2O$ (Alfa Aesar 12362) into 50 ml water, and 0.22 μm filtering. This was added to mTSB aliquots to achieve 0, 0.25, 0.50, and 1.0 ppm final concentrations. The pH of the media was then brought down to pH 4.5 by the addition of HCl to allow complete separation of the $Al^{3+}$ ion.

Spore Suspensions:

Spore powders of *Bacillus licheniformis* strain ENV 100 treated or not treated with GOSD were suspended in sterile water with 0.1% Octosol SLS (FT-SLS-246DRUM, Tiarco Chemical, Dalton, Ga.) within a sterile blender jar. Spores were suspended by blending for 5 second intervals for a total of at least 15 seconds or until the spores were completely suspended visually. This was performed such that the final concentration in the blender jar was $1\times10^{10}$ cfu/ml. From this spore suspension, 250 μl was transferred to tubes containing 4.75 ml mTSB to give a final concentration of $5\times10^8$ cfu/ml. These concentrations are determined by optimizations performed on each batch of spores to achieve a starting OD600 of approximately 0.6.

OD Germination Assay: Performed and calculated as in Example 6.

TABLE 8

Percent germination of *Bacillus licheniformis* spores over one hour with GOSD (GO+) and without (GO−) in the presence of 0, 0.25 ppm, 0.50 ppm and 1.0 ppm solutions of Aluminum ions.

| Time | GO+ 0 ppm | GO− 0 ppm | GO+ 0.25 ppm | GO− 0.25 ppm | GO+ 0.50 ppm | GO− 0.50 ppm | GO+ 1.00 ppm | GO− 1.00 ppm |
|---|---|---|---|---|---|---|---|---|
| 0:00 | 0 | 0 | 0 | 0 | 0 | 0 | 0 | 0 |
| 0:07 | 21% | 2% | 9% | 1% | 26% | 2% | 30% | 3% |
| 0:14 | 48% | 3% | 47% | 4% | 50% | 4% | 52% | 3% |
| 0:22 | 62% | 3% | 60% | 5% | 63% | 4% | 63% | 4% |
| 0:30 | 67% | 2% | 66% | 4% | 67% | 4% | 67% | 3% |
| 0:37 | 70% | 3% | 68% | 5% | 70% | 4% | 70% | 3% |
| 0:44 | 71% | 3% | 69% | 4% | 71% | 4% | 71% | 3% |
| 0:52 | 72% | 3% | 70% | 4% | 72% | 5% | 71% | 3% |
| 0:59 | 72% | 3% | 70% | 5% | 74% | 6% | 73% | 4% |
| 1:07 | 72% | 3% | 72% | 5% | 74% | 5% | 72% | 4% |

Conclusion: Treatment with GOSD enables *Bacillus licheniformis* spores to germinate faster and overcome the stress effects of various levels of Aluminum ions.

Example 9

Percent Germination of *Bacillus licheniformis* with and without GOSD in the Presence of Different Millimolar Solutions of Bile Salts Medium:

mTSB medium was prepared as above, but supplemented with NaCl to a final concentration of 50 mM to create an osmotically balanced media. A 80 mM bile salts stock solution was made by suspending 2.5 g sodium taurodeoxycholate (Sigma T0875), 1.1 g sodium glycodeoxycholate (Sigma G9910), and 0.346 g sodium deoxycholate (Sigma D5670) into 100 ml water, and 0.22 μm filtering. This was added to mTSB aliquots to achieve 0, 4, 6, and 8 mM final concentrations.

Spore Suspensions:

Spore powders of *Bacillus licheniformis* strain ENV 100 treated or not treated with GOSD were suspended in sterile water with 0.1% Octosol SLS (FT-SLS-246DRUM, Tiarco Chemical, Dalton, Ga.) within a sterile blender jar. Spores were suspended by blending for 5 second intervals for a total of at least 15 seconds or until the spores were completely suspended visually. This was performed such that the final concentration in the blender jar was $1 \times 10^{10}$ cfu/ml. From this spore suspension, 250 μl was transferred to tubes containing 4.75 ml mTSB to give a final concentration of $5 \times 10^8$ cfu/ml. These concentrations are determined by optimizations performed on each batch of spores to achieve a starting OD600 of approximately 0.6.

OD Germination Assay:

Performed and calculated as above.

TABLE 9

Percent germination of *Bacillus licheniformis* spores over one hour with GOSD (GO+) and without (GO−) in the presence of 0, 4 mM, 6 mM and 8 mM ppm solutions of Bile Salts.

| Time | GO+ 0 mM | GO− 0 mM | GO+ 4 mM | GO− 4 mM | GO+ 6 mM | GO− 6 mM | GO+ 8 mM | GO− 8 mM |
|---|---|---|---|---|---|---|---|---|
| 0:00 | 0 | 0 | 0 | 0 | 0 | 0 | 0 | 0 |
| 0:05 | 13% | 4% | 17% | 1% | 22% | 1% | 29% | 7% |
| 0:10 | 44% | 5% | 44% | 1% | 50% | 2% | 56% | 10% |
| 0:15 | 61% | 5% | 61% | 1% | 62% | 1% | 67% | 9% |
| 0:20 | 70% | 5% | 69% | 2% | 70% | 3% | 73% | 11% |
| 0:26 | 76% | 5% | 73% | 2% | 75% | 2% | 77% | 11% |
| 0:31 | 78% | 5% | 77% | 3% | 78% | 3% | 81% | 11% |
| 0:36 | 81% | 5% | 80% | 2% | 80% | 3% | 83% | 11% |
| 0:41 | 83% | 6% | 82% | 3% | 82% | 2% | 84% | 11% |
| 0:46 | 85% | 7% | 83% | 2% | 84% | 2% | 86% | 11% |
| 0:51 | 86% | 6% | 85% | 2% | 86% | 3% | 87% | 11% |
| 0:56 | 86% | 6% | 85% | 2% | 87% | 3% | 88% | 11% |
| 1:01 | 87% | 6% | 87% | 2% | 88% | 3% | 90% | 11% |
| 1:06 | 88% | 7% | 89% | 3% | 89% | 3% | 90% | 11% |

Conclusion: Treatment with GOSD enables *Bacillus licheniformis* spores to germinate faster and overcome the stress effects of various levels of bile salts which can be encountered in a gastrointestinal tract.

Example 10

Average Growth of Three Replicates of *Bacillus licheniformis* with or without GOSD in Defined Potassium Phosphate Medium and 2% Glucose

*Bacillus licheniformis* strain ENV 431 GO+ spores were treated with GOSD (procedure described earlier). As a control were used GO− spores from the same culture that were spray dried without using GOSD. The growth test was performed in Minimal Salts Medium supplemented with 2% glucose.

Medium

The medium was prepared by dissolving $(NH_4)_2SO_4$ (1.26 g/L), $MgCl_2$ (0.81 g/L), $CaCl_2$ (0.15 g/L), NaCl (0.05 g/L) in distilled water and adding 1 ml/L 1000× Trace Mineral Mix ($MnSO_4$ (0.85 g/50 ml), $ZnSO_4$ (0.15 g/50 ml), $FeSO_4 \times 7H_2O$ (0.15 g/50 ml), Thiamino-hydrochloride (0.05 g/50 ml). Prepared solution was poured into flasks (90 ml/flask) and autoclaved at 121° C. for 40 min. Before inoculation the medium was supplemented with 4 ml of filter sterilized solution of 25× Potassium Phosphate ($K_2HPO_4$ (3.44 g/50 ml), $KH_2PO_4$ (2.81 g/50 ml)) and 2 ml of 50×(100 g/200 ml) glucose to 2% final concentration.

Growth of Bacillus licheniformis Cells

Amount of spores used for inoculation was determined using GO− and GO+ spore powder counts. Concentrated (1000×) Bacillus licheniformis strain ENV 431 spore suspensions were prepared by blending spores in the sterile blender jars using sterile water and added to the flasks with medium to the concentrations indicated in the table below as 0 h. The counts of initial culture were obtained by performing dilutions and plate counts of blended spore suspensions. There were 3 flasks prepared for each spore sample.

The flasks were incubated at 30° C., 150 rpm and grown for 48 h. The samples were taken and plate counts done at 24 h and 48 h.

TABLE 10

Average growth of three replicates of Bacillus licheniformis with GOSD (GO+) or without GOSD (GO−)in minimal potassium phosphate medium and 2% glucose. Data shown is in cfu/ml.

|  | 0 hour | 24 hours | 48 hours |
|---|---|---|---|
| B. licheniformis GO− | $1.88 \times 10^3$ | $2.20 \times 10^4$ | $9.4 \times 10^4$ |
| B. licheniformis GO+ | $1.46 \times 10^3$ | $7.95 \times 10^4$ | $3.65 \times 10^5$ |

Conclusion: GOSD treatment significantly enhanced Bacillus licheniformis germination and growth rate.

Example 11

Growth of Bacillus licheniformis Over a Two Day Period; Comparing Treatments with or without GOSD in the Presence of Different Concentrations of NaCl Medium:

mTSB was prepared as above, but with sodium chloride (Amresco X190) added to induce osmotic stress where appropriate such that the final concentrations were 0, 0.5, 1.0, or 1.5 M (0, 29.22, 58.44, or 87.66 g/L respectively). The media was heated, aliquoted to flasks, and autoclaved.

Plate Count Agar (PCA) (BD 247910) was prepared according to the manufacturer's instructions: 23.5 g of powder suspended in 1 L of water, bring to boil with frequent agitation, aliquot into glass jars, and autoclave. Media jars were cooled in a 45° C. water bath until needed. The manufacturer of the powder reports the following contents for PCA per liter:

Pancreatic Digest of Casein: 5.0 g
Yeast Extract: 2.5 g
Dextrose: 1.0 g
Agar: 15.0 g Spore Suspensions:

Spore powders of Bacillus licheniformis strain ENV100 treated or not treated with GOSD were suspended in sterile water with 0.1% Octosol SLS (FT-SLS-246DRUM, Tiarco Chemical, Dalton, Ga.) within a sterile blender jar. Spores were suspended by blending for 5 second intervals for a total of at least 15 seconds or until the spores were completely suspended visually followed by serial dilutions in sterile water. This was performed such that the final concentration in the culture flasks was $1 \times 10^2$ cfu/ml.

Quantification:

Flasks were incubated at 37° C. shaking at 150 rpm for 28 hours ("1 day") or 50 hours ("2 days"). Aliquots from each flask were serially diluted into petri dishes with PCA cooled to <45° C. poured on top, swirled, and allowed to solidify. Plates were inverted and incubated for approximately 24 hours at 37° C. Colonies were counted and concentrations calculated based on dilutions. Approximately 10 μl samples from each flask were also streaked on PCA plates to test for purity.

TABLE 11

Growth of Bacillus licheniformis treated with GOSD (GO+) when challenged by osmotic stress from salt solution.

| Day | GO+ or− | Molar | cfu/ml |
|---|---|---|---|
| 1 | GO+ | 0 | 1.05E+06 |
| 1 | GO− | 0 | 7.33E+03 |
| 1 | GO+ | 0.5 | 3.60E+06 |
| 1 | GO− | 0.5 | 5.00E+06 |
| 1 | GO+ | 1.0 | 3.00E+05 |
| 1 | GO− | 1.0 | 2.31E+05 |
| 1 | GO+ | 1.5 | 1.22E+04 |
| 1 | GO− | 1.5 | 1.50E+02 |
| 2 | GO+ | 0 | 8.17E+06 |
| 2 | GO− | 0 | 4.90E+05 |
| 2 | GO+ | 0.5 | 7.03E+06 |
| 2 | GO− | 0.5 | 8.43E+06 |
| 2 | GO+ | 1.0 | 2.07E+06 |
| 2 | GO− | 1.0 | 3.50E+06 |
| 2 | GO+ | 1.5 | 4.33E+05 |
| 2 | GO− | 1.5 | 1.53E+02 |

Conclusion: GOSD treatment significantly enhanced germination and growth of Bacillus licheniformis under osmotic salt stress.

Example 12

Protease Activity of Bacillus subtilis Strain ENV 923

Bacillus subtilis strain ENV 923 spores treated with GOSD (GO+) as described earlier, and non-treated (GO−) were used for the protease activity test.

Medium

Chemically Defined Salt Medium (CDSM) was used for cell propagation in a protease test. Medium was prepared by dissolving base solution components (g/L): $(NH_4)SO_4$, 1.26 g; L-glutamic acid, 1.18 g; $MgCl_2$, 0.81; $CaCl_2$, 0.155 and 85% L-lactic acid (0.530 ml/L) in distilled water and adding 1 ml/L of 1000× Trace Mineral Mix (g/50 ml). Flasks with base solution (48 ml/flask) were autoclaved for 40 min. Before inoculation 2 ml of separately prepared filter sterilized 25× buffer solution with glucose (g/50 ml): MOPS, 11.6; $KH_2PO_4$, 0.6; glucose, 4.5 were added.

Growth of Bacillus subtilis ENV923 Cells

The amount of spores used for inoculation was determined using GO− and GO+ spore powder counts. Concentrated (1000×) Bacillus subtilis strain ENV923 spore suspensions were prepared by blending spores in the sterile blender jars using sterile 0.01 M Potassium Phosphate buffer, pH 7.0 and added to the flasks at the concentration of about $1 \times 10^4$ cfu/ml. The counts of initial culture were confirmed by performing dilutions and plate counts of blended spore suspensions. There were 3 flasks prepared for each spore sample.

The flasks were incubated at 30° C., 150 rpm, and samples were taken at 48 h.

Protease Activity Assay

Protease activity assay was carried out on cell supernatants using casein as substrate and Folin & Ciocalateu's Phenol reagent that reacts with tyrosine and facilitates blue color development. Protease activity unit was defined as amount of enzyme that liberates 1 µg of tyrosine in one minute. Amount of tyrosine in test tubes was determined by measuring $OD_{650}$ in a Jenway 7305 spectrophotometer and calculating liberated tyrosine using a standard curve.

Reagents

Reagent 1: 0.05 M Potassium Phosphate Buffer, pH 7.0

0.1 M Potassium Phosphate buffer, pH 7.0 (prepared as described in Example 1) was diluted to at the ratio 1:1 with distilled water to obtain 0.05 M Potassium Phosphate buffer, pH 7.0

Reagent 2: 0.65% Casein Solution 0.65 g of casein were dissolved in 80 ml of 0.05 M Potassium Phosphate buffer, pH 7.0, heated to bring casein into solution, and the final volume brought to 100 ml with 0.05 M Potassium Phosphate buffer, pH 7.0.

Reagent 3: 15% Trichloroacetic Acid (TCA)

15 g of TCA were dissolved in distilled water and the final volume brought to 100 ml.

Reagent 4: 20% $Na_2CO_3$ 20 g of $Na_2CO_3$ dissolved in distilled water and final volume brought to 100 ml.

Protease Assay 10 ml of culture were centrifuged and supernatant filtered through 0.2 µm filter into sterile tubes.

3 ml of filtered supernatant were mixed with 3 ml of 0.65% casein solution and put into 37° C. water bath for 1 h.

Reaction was stopped by adding 6 ml of 15% TCA and samples centrifuged for 5 min.

0.5 ml of each sample was mixed with 1 ml of 20% $Na_2CO_3$, followed by 0.5 ml of Folin & Ciolcallieu's Phenol reagent addition and incubation for 20 min at room temperature to allow blue color development.

3 ml of distilled water were added to each sample and after mixing the $OD_{650}$ was measured.

To calculate protease activity the standard curve for tyrosine was prepared obtaining dilution series of tyrosine dissolved in distilled water, treating them to the same conditions as the culture samples, and measuring $OD_{650}$.

TABLE 12

Protease production of *Bacillus subtilis* treated with GOSD (GO+) versus control (GO-)

| *Bacillus subtilis* | | Protease activity units |
|---|---|---|
| 54 h. | GO+ | 71.5 |
|  | GO- | 40 |

Conclusion: Treatment of *Bacillus subtilis* spores with GOSD enables greater production of enzymes such as protease.

Example 13

Germination of *Streptomyces viridochromogenes* in the Presence of Germinative Compounds

*Streptomyces* viridochromogenes spores were harvested from plates by pouring 10 ml of TX buffer (0.05 M Tris-HCl buffer, pH 7.3 with 0.001% Tween 80) and removing the spores with a sterile cotton swab. Spore suspensions from plates were poured into sterile 50 ml tubes. When spore suspensions of all samples were obtained, heat shock was performed by putting the tubes with spore suspensions into a heat block, allowing the temperature to reach 55° C., and maintain the temperature at 55° C. for 10 min. After heat shock spore suspensions were cooled in ice water for 5 min and spun down for 30 min. Supernatant was poured off, spores re-suspended in 25 ml 0.02 M Potassium Phosphate buffer, pH 7.0 at 4° C. and spun down for 15 min. After pouring off supernatant, spores were re-suspended in 20 ml of 0.02 M Potassium Phosphate buffer, pH 7.0 and vigorously mixed to obtain the spore suspension that was used in the experiment.

Samples were prepared by mixing 1.5 ml of 2× germinant blend with 1.5 ml spore suspension. All germinant blends were prepared in distilled water as 2×50 ml solutions. Calcium chloride was prepared as a 100× solution (0.4 g/10 ml) and 20 µl were added to 10 ml of 2× germinant blends. The final concentrations of the germinative compounds were as follows: 0.89 mg/ml of L-alanine; 1.17 mg/ml of L-valine, 13.2 mg/ml of L-asparagine; 2.25 mg/ml of glucose; and 2.25 mg/ml of fructose. After measuring initial OD600, samples were transferred to a 30° C. water bath and OD600 was measured at 15 min intervals for 90 min to determine germination rates.

TABLE 13

ENV 151 (*Streptomyces viridochromogenes*) % Reduction in Optical Density

| Ion/Germinant treatment | 0 | 15 | 30 | 45 | 60 | 75 | 90 |
|---|---|---|---|---|---|---|---|
| 0.01M KPO4 | 0 | 1.0% | 2.0% | 5.4% | 6.2% | 4.9% | 5.4% |
| 0.01M KPO4, CaCl$_2$ | 0 | 7.3% | 3.4% | 6.1% | 6.1% | 8.0% | 9.3% |
| 0.01M KPO4, CaCl$_2$, L-Ala | 0 | 1.8% | 5.2% | 12.2% | 11.9% | 14.2% | 17.6% |
| 0.01M KPO4, CaCl$_2$, L-Val | 0 | 2.0% | 4.9% | 11.2% | 7.8% | 14.4% | 18.0% |
| 0.01M KPO4, CaCl$_2$, L-Asn | 0 | 2.0% | 6.1% | 8.8% | 11.7% | 8.0% | 9.0% |
| 0.01M KPO4, CaCl$_2$, L-Ala, L-Asn | 0 | 7.7% | 12.1% | 14.4% | 19.8% | 20.4% | 18.6% |
| 0.01M KPO4, CaCl$_2$, L-Ala, L-Asn, glucose | 0 | 8.2% | 11.7% | 14.5% | 20.1% | 19.4% | 20.7% |
| 0.01M KPO4, CaCl$_2$, glucose | 0 | 7.0% | 8.8% | 7.0% | 10.5% | 12.6% | 13.2% |
| 0.01M KPO4, CaCl$_2$, glucose, fructose | 0 | 5.9% | 8.3% | 12.0% | 12.7% | 14.6% | 14.6% |
| 0.01M KPO4, CaCl$_2$, L-Ala, L-Asn, glucose, fructose | 0 | 11.7% | 14.0% | 17.7% | 20.4% | 22.2% | 22.4% |

Conclusion: Treatment of *Streptomyces viridochromogenes* spores with germinative compounds enhanced germination.

Example 14

Comparison of Germination Rates Between Intimate Mixtures and Conventional Mixing of Bacterial Spores and Germinative Compounds In order to compare the germination rate of the spores of intimate mixtures with that of spores conventionally mixed with a germinant, the following treatments are performed:

A. Formation of an Intimate Mixture: Spores of *B. subtilis, B. amyloliquefaciens, B. brevis, B. cereus, B. coagulans, B. firmus, B. laterosporus, B. licheniformis, B. megaterium, B. mycoides, B. popilliae, B. polymyxa, B. pumilus, B. thuringiensis, Pasteuria penetrans, Pasteuria thornei, Pasteuria nishizawae, Streptomyces viridochromogenes, Streptomyces griseoviridis, Streptomyces lydicus, Streptomyces plicatus, Streptomyces sindeneusis, Streptomyces rochei, Streptomyces alni, Streptomyces viridis, Streptomyces thermovulgaris, Streptomyces griseus, Streptomyces acidiscabies, Steptomyces aureofaciens, Streptomyces galbus, Streptomyces microflavus,* and *Streptomyces aureofacien* are dried with L-alanine, L-valine, L-proline, L-leucine, L-cysteine, L-threonine, L-glutamine, L-asparagine or L-phenylalanine being introduced to the spore mass immediately prior to drying as a solution containing 0.044 grams of the amino acid per milliliter of distilled water. The intimate mixture produced is germinated by subsequent introduction in a solution consisting of 0.01 M phosphate buffer in distilled water with resultant pH 7.

B. Conventional Mixing of Spores with a Germinant: Spores of *B. subtilis, B. amyloliquefaciens, B. brevis, B. cereus, B. coagulans, B. firmus, B. laterosporus, B. licheniformis, B. megaterium, B. mycoides, B. popilliae, B. polymyxa, B. pumilus, B. thuringiensis, Pasteuria penetrans, Pasteuria thornei, Pasteuria nishizawae, Streptomyces viridochromogenes, Streptomyces griseoviridis, Streptomyces lydicus, Streptomyces plicatus, Streptomyces sindeneusis, Streptomyces rochei, Streptomyces alni, Streptomyces viridis, Streptomyces thermovulgaris, Streptomyces griseus, Streptomyces acidiscabies, Steptomyces aureofaciens, Streptomyces galbus, Streptomyces microflavus,* and *Streptomyces aureofacien* are hydrated and dried. Such spores are germinated by the introduction in a solution consisting of 0.01 M phosphate buffer in distilled water with resultant pH 7, and 0.0001 grams of L-alanine, L-valine, L-proline, L-leucine, L-cysteine, L-threonine, L-glutamine, L-asparagine or L-phenylalanine per milliliter of solution.

C. Germination of Spores Alone: Spores of *B. subtilis, B. amyloliquefaciens, B. brevis, B. cereus, B. coagulans, B. firmus, B. laterosporus, B. licheniformis, B. megaterium, B. mycoides, B. popilliae, B. polymyxa, B. pumilus, B. thuringiensis, Pasteuria penetrans, Pasteuria thornei, Pasteuria nishizawae, Streptomyces viridochromogenes, Streptomyces griseoviridis, Streptomyces lydicus, Streptomyces plicatus, Streptomyces sindeneusis, Streptomyces rochei, Streptomyces alni, Streptomyces viridis, Streptomyces thermovulgaris, Streptomyces griseus, Streptomyces acidiscabies, Steptomyces aureofaciens, Streptomyces galbus, Streptomyces microflavus,* and *Streptomyces aureofacien* are hydrated and dried. The spores are subsequently introduced into a solution consisting of 0.01 M phosphate buffer in distilled water with resultant pH 7.

The germination of spores resulting for each such treatment is measured by the percent drop in optical density or by counting the number of germinated spores under a microscope. It is found that the intimately mixed compositions germinate more rapidly than their corresponding conventionally mixed equivalent.

What is claimed is:

1. A dried intimate mixture comprising a bacterial spore and L-alanine, wherein the bacterial spore and the L-alanine in the intimate mixture are dried together such that the bacterial spore and the L-alanine are maintained in proximate position until they reach an environment conducive to germination, and wherein the bacterial spore in the intimate mixture germinates more rapidly than a bacterial spore that is not intimately mixed with the L-alanine.

2. The mixture of claim 1 wherein the spore is selected from the group consisting of *B. alcalophilus, B. alvei, B. amyloliquefaciens, B. aneurinolyticus, B. anthracis, B. aquaemaris, B. atrophaeus, B. boronophilus, B. brevis, B. caldolyyicus, B. centrosporus, B. cereus, B. circulans, B. clausii, B. coagulans, B. firmus, B. flavothermus, B. fusiformis, B. globigii, B. infernus, B. larvae, B. laterosporus, B. lentus, B. lentimorbus, B. licheniformis, B. megaterium, B. mesentericus, B. mucilaginosus, B. mycoides, B. natto, B. pantothenicus, B. popilliae, B. polymyxa, B. pseudoanthracis, B. pumilus, B. schlegelii, B. simplex, B. sphaericus, B. sporothermodurans, B. stearothermophilus, B. subtilis, B. thermoglucosidasius, B. thuringiensis, B. vulgatis,* and *B. weihenstephanensis.*

3. The mixture of claim 1 wherein said composition is a mixture selected from the group consisting of L-alanine+*Bacillus subtilis*, L-alanine+*Bacillus licheniformis*, L-alanine+*Bacillus pumilus*, L-alanine+*Bacillus amyloliquefaciens*, L-alanine+*Bacillus coagulans*, L-alanine+*Bacillus cereus*, L-alanine+*Bacillus clausii*, L-alanine+glucose+fructose+potassium ions (GFK)+*Bacillus subtilis*, L-alanine+glucose+fructose+potassium ions (GFK)+*Bacillus licheniformis*, L-alanine+glucose+fructose+potassium ions (GFK)+*Bacillus pumilus*, L-alanine+glucose+fructose+potassium ions (GFK)+*Bacillus amyloliquefaciens*, L-alanine+glucose+fructose+potassium ions (GFK)+*Bacillus coagulans*, L-alanine+glucose+fructose+potassium ions (GFK)+*Bacillus cereus*, L-alanine+glucose+fructose+potassium ions (GFK)+*Bacillus clausii*, L-alanine+inosine+*Bacillus subtilis*, L-alanine+inosine+*Bacillus licheniformis*, L-alanine+inosine+*Bacillus pumilus*, L-alanine+inosine+*Bacillus amyloliquefaciens*, L-alanine+inosine+*Bacillus coagulans*, L-alanine+inosine+*Bacillus cereus*, and L-alanine+inosine+*Bacillus clausii*.

4. The mixture of claim 1 wherein the spore is selected from the group consisting of *B. subtilis, B. amyloliquefaciens, B. licheniformis, B. megaterium,* and *B. pumilus.*

5. A composition comprising the dried intimate mixture of claim 1.

6. The composition of claim 5 wherein the spore is selected from the group consisting of *B. alcalophilus, B. alvei, B. amyloliquefaciens, B. aneurinolyticus, B. anthracis, B. aquaemaris, B. atrophaeus, B. boronophilus, B. brevis, B. caldolyyicus, B. centrosporus, B. cereus, B. circulans, B. clausii, B. coagulans, B. firmus, B. flavothermus, B. fusiformis, B. globigii, B. infernus, B. larvae, B. laterosporus, B. lentus, B. lentimorbus, B. licheniformis, B. megaterium, B. mesentericus, B. mucilaginosus, B. mycoides, B. natto, B. pantothenicus, B. popilliae, B. polymyxa, B. pseudoanthracis, B. pumilus, B. schlegelii, B. simplex, B. sphaericus, B. sporothermodurans, B. stearothermophilus, B. subtilis, B. thermoglucosidasius, B. thuringiensis, B. vulgatis,* and *B. weihenstephanensis.*

7. The composition of claim 5 wherein said composition is a mixture selected from the group consisting of L-alanine+*Bacillus subtilis*, L-alanine+*Bacillus licheniformis*, L-alanine+*Bacillus pumilus*, L-alanine+*Bacillus amyloliquefaciens*, L-alanine+*Bacillus coagulans*, L-alanine+*Bacillus cereus*, L-alanine+*Bacillus clausii*, L-alanine+glucose+fructose+potassium ions (GFK)+*Bacillus subtilis*, L-alanine+glucose+fructose+potassium ions (GFK)+*Bacillus licheniformis*, L-alanine+glucose+fructose+potassium ions (GFK)+*Bacillus pumilus*, L-alanine +glucose+fructose+potassium ions (GFK)+*Bacillus amyloliquefaciens*, L-alanine +glucose+fructose+potassium ions (GFK)+*Bacillus coagulans*, L-alanine+glucose+fructose+potassium ions (GFK)+ *Bacillus cereus*, L-alanine+glucose+fructose+potassium ions (GFK)+*Bacillus clausii*, L-alanine+inosine+*Bacillus subtilis*, L-alanine+inosine+*Bacillus licheniformis*, L-alanine+inosine+*Bacillus pumilus*, L-alanine+inosine+*Bacillus amyloliquefaciens*, L-alanine+inosine+*Bacillus coagulans*, L-alanine+inosine+*Bacillus cereus*, and L-alanine+inosine+*Bacillus clausii*.

8. The composition of claim 5 wherein such composition further comprises an enteric coating.

9. The composition of claim 5 wherein the spore is selected from the group consisting of *B. subtilis, B. amyloliquefaciens, B. licheniformis, B. megaterium*, and *B. pumilus*.

10. The mixture of claim 1, wherein the L-alanine is formulated, prior to drying, at a concentration of 0.0003 mg/mL to 30 mg/mL.

11. A method for preparing a dried intimate mixture comprising a bacterial spore and L-alanine, the method comprising:
    a) preparing a solution comprising a bacterial spore and L-alanine; and
    b) drying the solution to obtain a dried intimate mixture comprising a bacterial spore and L-alanine,
    wherein the bacterial spore and the L-alanine in the intimate mixture are dried together such that the bacterial spore and the L-alanine are maintained in proximate position until they reach an environment conducive to germination, and wherein the bacterial spore in the intimate mixture germinates more rapidly than a bacterial spore that is not intimately mixed with the L-alanine.

12. The method of claim 11, wherein the spore is selected from the group consisting of *B. alcalophilus, B. alvei, B. amyloliquefaciens, B. aneurinolyticus, B. anthracis, B. aquaemaris, B. atrophaeus, B. boronophilus, B. brevis, B. caldolyyicus, B. centrosporus, B. cereus, B. circulans, B. clausii, B. coagulans, B. firmus, B. flavothermus, B. fusiformis, B. globigii, B. infernus, B. larvae, B. laterosporus, B. lentus, B. lentimorbus, B. licheniformis, B. megaterium, B. mesentericus, B. mucilaginosus, B. mycoides, B. natto, B. pantothenicus, B. popilliae, B. polymyxa, B. pseudoanthracis, B. pumilus, B. schlegelii, B. simplex, B. sphaericus, B. sporothermodurans, B. stearothermophilus, B. subtilis, B. thermoglucosidasius, B. thuringiensis, B. vulgatis*, and *B. weihenstephanensis*.

13. The method of claim 11, wherein the spore is selected from the group consisting of *B. subtilis, B. amyloliquefaciens, B. licheniformis, B. megaterium*, and *B. pumilus*.

14. A dried intimate mixture produced by the method of claim 11.

15. A method for increasing the germination of bacterial spores, comprising:
    a) preparing a solution comprising a bacterial spore and L-alanine; and
    b) drying the solution to obtain a dried intimate mixture comprising a bacterial spore and L-alanine, wherein the bacterial spore and the L-alanine in the intimate mixture are dried together such that the bacterial spore and L-alanine are maintained in proximate position until they reach an environment conducive to germination of the bacterial spores; and
    c) exposing the intimate mixture to an environment conducive to germination of the bacterial spores, wherein the germination of the bacterial spores in the intimate mixture is increased relative to a corresponding bacterial spore formulation that lacks L-alanine.

* * * * *